United States Patent
Herzl et al.

(10) Patent No.: US 9,291,608 B2
(45) Date of Patent: Mar. 22, 2016

(54) CALIBRATION METHOD FOR DISTRIBUTED SENSOR SYSTEM

(71) Applicant: Aclima Inc., San Francisco, CA (US)

(72) Inventors: Davida Herzl, San Francisco, CA (US);
Gabriel Risk, San Francisco, CA (US);
Roland Herzl, San Francisco, CA (US);
Tobe Corazzini, Newcastle, CA (US);
Stanley Hu, San Francisco, CA (US)

(73) Assignee: Aclima Inc., San Francisco, CA (US)

( * ) Notice: Subject to any disclaimer, the term of this patent is extended or adjusted under 35 U.S.C. 154(b) by 466 days.

(21) Appl. No.: 13/800,199

(22) Filed: Mar. 13, 2013

(65) Prior Publication Data

US 2014/0278186 A1    Sep. 18, 2014

(51) Int. Cl.
*G01N 33/00*    (2006.01)

(52) U.S. Cl.
CPC .................. *G01N 33/0006* (2013.01)

(58) Field of Classification Search
CPC .................................................. G01N 33/0006
USPC .......................................................... 702/104
See application file for complete search history.

(56) References Cited

U.S. PATENT DOCUMENTS

| | | | |
|---|---|---|---|
| 5,428,776 A | 6/1995 | Rothfield | |
| 6,128,617 A | 10/2000 | Lowry | |
| 6,941,193 B2 | 9/2005 | Frecska et al. | |
| 7,046,166 B2 | 5/2006 | Pedyash et al. | |
| 7,146,356 B2 | 12/2006 | Choi et al. | |
| 7,188,090 B2 | 3/2007 | Kim et al. | |
| 7,302,313 B2 | 11/2007 | Sharp et al. | |
| 7,849,048 B2 | 12/2010 | Langseth et al. | |
| 8,289,992 B2 | 10/2012 | Fujiwara et al. | |
| 8,294,715 B2 | 10/2012 | Patel et al. | |
| 8,326,662 B1 | 12/2012 | Byrne et al. | |
| 8,355,981 B2 | 1/2013 | West | |
| 8,370,386 B1 | 2/2013 | Wang et al. | |
| 8,395,625 B2 | 3/2013 | Buck | |
| 2002/0128998 A1 | 9/2002 | Kil et al. | |
| 2005/0190058 A1 | 9/2005 | Call | |
| 2009/0172090 A1 | 7/2009 | Lit | |
| 2010/0138751 A1* | 6/2010 | Kumar et al. | 715/736 |

FOREIGN PATENT DOCUMENTS

EP    0797162    9/1997

* cited by examiner

*Primary Examiner* — Bryan Bui
(74) *Attorney, Agent, or Firm* — Van Pelt, Yi & James LLP

(57) ABSTRACT

Methods of calibrating sensors in a distributed sensor system including a set of spatially distributed base units in communication with a central server over a data network include using a reference sensor, using a reference base unit, using crowd-sourced calibration, using sensor data collected in the same base unit, using sensor cross-sensitivity, or using sensor data from known environmental conditions.

16 Claims, 8 Drawing Sheets

Calibration Data Table — 200

| Sensor ID | Board ID | Calibration Values | Valid Date |
|---|---|---|---|
|  |  |  | (start), (end) |
|  |  |  |  |
|  |  |  |  |
|  |  |  |  |

FIG. 4

Calibration Data Table

| Sensor ID | Board ID | Sensor Type | Calibration Values | Valid Date | Valid Indicator |
|---|---|---|---|---|---|
| | | | | (start), (end) | |
| | | | | | |
| | | | | | |
| | | | | | |

FIG. 8

CALIBRATION METHOD FOR DISTRIBUTED SENSOR SYSTEM

BACKGROUND OF THE INVENTION

Air quality is a measure of the condition of air relative to the requirements of human need or purpose. Outdoor air quality monitoring is performed to measure the levels of pollutants in the air so as to detect potential harmful air pollution. Outdoor air quality monitoring is typically carried out using monitoring station installations in various physical locations. These monitoring stations measure the presence of contaminants in the air, such as carbon monoxide, ozone, particulate matter, sulphur dioxide ($SO_2$) and carbon dioxide ($CO_2$). Indoor air quality monitoring is becoming a matter of interest as the air in enclosed spaces, such as home, schools or workplaces, can also be polluted. Conventional air quality monitors are expensive and require complex calibration procedure to ensure accurate functions.

BRIEF SUMMARY OF THE INVENTION

Methods of calibrating sensors in a distributed sensor system including a set of spatially distributed base units in communication with a central server over a data network include using a reference sensor, using a reference base unit, using crowd-sourced calibration, using sensor data collected in the same base unit, using sensor cross-sensitivity, or using sensor data from known environmental conditions.

BRIEF DESCRIPTION OF THE DRAWINGS

Various embodiments of the invention are disclosed in the following detailed description and the accompanying drawings.

FIG. 4 illustrates the organization of a calibration data table in embodiments of the present invention.

FIG. 8 illustrates the organization of a calibration data table in embodiments of the present invention.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
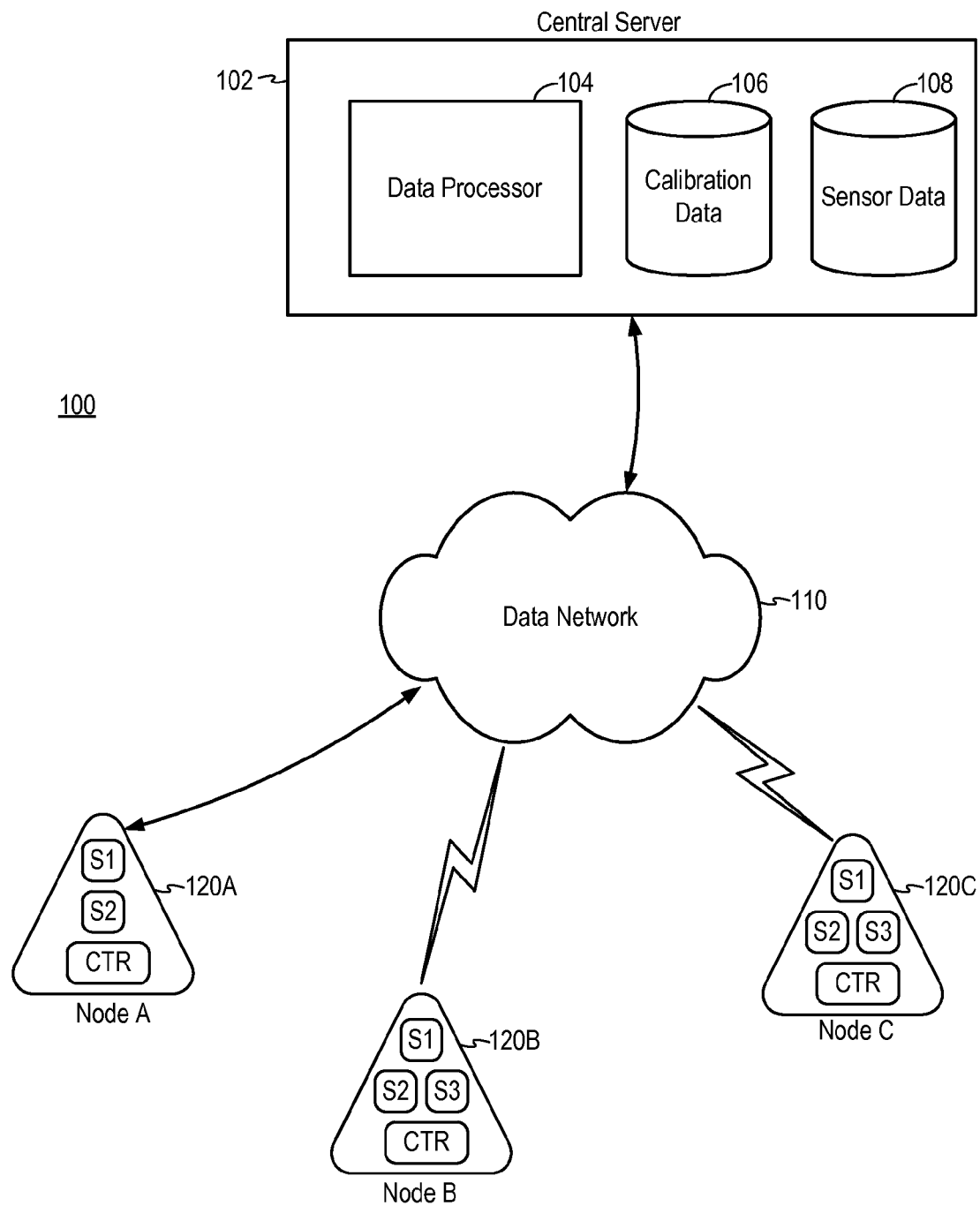
FIG. 1 is a system diagram illustrating an embodiment of a distributed sensor system for measuring air quality in an environment.

FIG. 1 is a system diagram illustrating an embodiment of a distributed sensor system for measuring air quality in an environment. Referring to FIG. 1, a distributed sensor system 100 including a set of spatially distributed base units 120, also referred to as "sensor nodes" or "nodes," configured to obtain measurements from the environment. In FIG. 1, sensor nodes A to C (120A to 120C) are shown. The sensor nodes in system 100 may be deployed in an indoor location or an outdoor location or both for monitoring the local air quality. In some embodiments, a set of sensor nodes are strategically deployed in a location to obtain sufficient amount of measurements to assess the air quality in a location. For example, in one embodiment, a set of sensor nodes are spatially dispersed in a building, such as a workplace or a factory, to monitor the air quality in the building.

Each base unit 120 includes one or more sensor modules (S#) and a controller (CTR) which incorporates therein a transceiver. A sensor module S# incorporates a sensor for detecting a specific air quality parameter. The sensor modules may include different types of sensors for sensing different air quality parameters. A set of base units 120 deployed in an installation may be configured with sensor modules with the same sensor type. For example, nodes A, B and C all include sensor modules S1 and S2. A set of base units 120 may also be configured with sensor modules with different sensor types. For example, nodes B and C include the sensor module S3 and not Node A. A salient feature of the base unit 120 in the distributed sensor system of the present invention is that the base unit is configurable to allow any desired types of sensors to be incorporated for measuring the desired environment parameters, as will be described in more detail below.

Each of the base units 120 includes a transceiver to communicate with a central server 102 through a data network 110. The base units 120 may employ wired communication, such as Ethernet, or wireless communications, such as radio frequency (RF), WiFi, ZigBee or other low power short-range wireless communication protocols. The controller CTR controls the sensing and communication functions of the base unit.

Central server 102 includes a data processor 104, a calibration data database 106, and a sensor data database 108. Central server 102 stores in the sensor data database 108 raw sensor data received from the base units 120 over the data network 110. Data processor 104 is configured to process the raw sensor data using calibration data stored in the calibration database 106 to generate calibrated sensor data which can then be used to assess the air quality at the installation where sensor nodes 120 are deployed. The calibrated sensor data may also be stored in the sensor data database 108. The calibrated sensor data, as well as the raw sensor data, may be accessible through one or more application programming interface (API) to allow users to monitor the air quality measurements obtained by the distributed sensor system 100.

Another salient feature of the distributed sensor system of the present invention is that each sensor module provides raw sensor data to the central server to be stored and processed. In the present description, raw sensor data refers to sensor data that has not been modified or calibrated based on performance characteristics of the particular sensor that generated the sensor data. Most sensors have certain amount of non-linearity characteristics over time and sensors need to be calibrated for the non-linearity or performance drift over time. Typically, a sensor may have gain or offset that drifts over time as the sensor is being used in an environment. Conventional sensors are often calibrated periodically, such as annually, and the calibration data, such as a gain correction value and an offset correction value, for the sensor is stored with the sensor itself and sensor data is modified using the calibration data as the sensor data is being generated by the sensor. In the conventional sensors, when a sensor's characteristics drift over time before the next calibration update, the calibration data may no longer be accurate for that sensor. However, the sensor will continue to use the inaccurate calibration data to calibrate or modify the sensor data. Thus, conventional sensors may end up generating sensor data that has embedded calibration error and the sensor data is permanently corrupted. In embodiments of the present invention, the distributed sensor system 100 implements a centralized backend calibration method where the base unit 120 reports raw sensor data that have not been modified to the central server 102. Calibration of the raw sensor data is performed at the central server 102 to generate calibrated sensor data using calibration data stored at the central server. The availability of the raw sensor data allows the central server to generate calibrated sensor data using updated or corrected calibration data so that accuracy of the sensor measurement can be assured. More importantly, when calibration data for a sensor is found to be inaccurate later on and new calibration data is generated, the central sever may regenerate the calibrated sensor data by retrieving the raw sensor data for that sensor and calibrating the raw sensor data again using updated calibration data. In this manner, historic sensor data can be corrected if the calibration data used was found to be inaccurate. Correction of historic sensor data is not possible in conventional sensors because the calibration was done at the sensor and raw sensor data is typically not available. The centralized backend calibration method in the distributed sensor system of the present invention will be described in more detail below.

In FIG. 1, the calibration data and the sensor data are shown as being stored in two databases. The two databases can be two physical databases or two logical databases. The exact configuration of the two databases is not critical to the practice of the present invention. The storage of the calibration data and the sensor data can be made in one physical data storage or multiple physical data storage.

Figure 2:
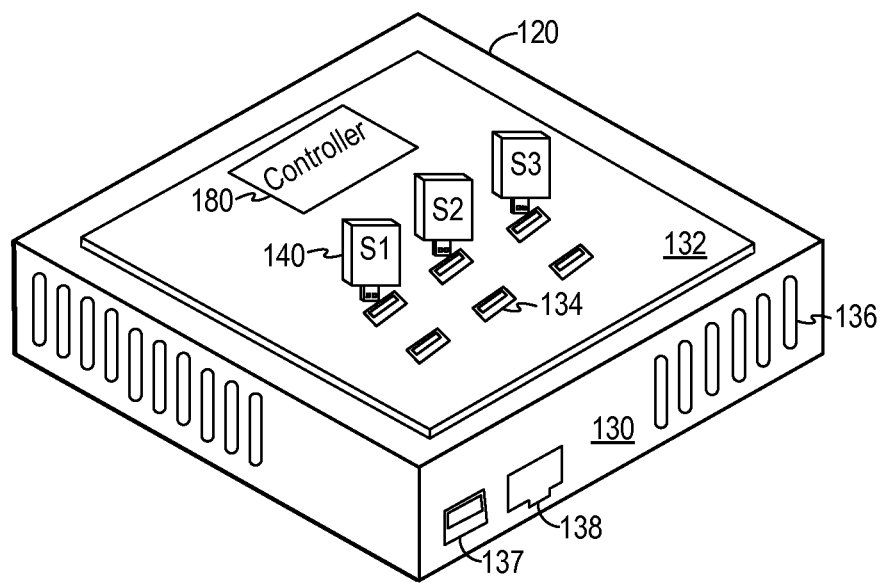
FIG. 2 illustrates an exposed perspective view of a base unit in embodiments of the present invention.

FIG. 2 illustrates an exposed perspective view of a base unit in embodiments of the present invention. Referring to FIG. 2, a base unit 120, or sensor node 120, is enclosed in a housing 130 having air vents 136 formed there on to enable air diffusion or air flow into the housing to reach the sensors housed therein. In most embodiments, base unit 120 is enclosed entirely by housing 130. In the present illustration, the top of housing 130 is omitted to illustrate the internal construction of the base unit. Base unit 120 includes a printed circuit board 132 on which a controller 180 is formed. The controller 180 may include one or more integrated circuits formed on the printed circuit board 132. For example, controller 180 may include a processor integrated circuit and a memory integrated circuit for supporting the operation of the base unit. Controller 180 may also include a transceiver circuit to enable the base unit to communicate with a data network. Controller 180 may be configured to provide wired communication or wireless communication with a data network. To support wired communication, base unit 120 may include data ports, such as USB port 137 and Ethernet port 138, to connect to a data network through wired connections. The USB port 137 may also be used to daisy chain two or more base units together, such as for calibration purposes, as will be explained in more detail below. To support wireless communication, base unit 120 may include an antenna (not shown).

In embodiments of the present invention, base unit 120 incorporates therein one or more sensor modules 140. Each sensor module 140 includes a sensor of a particular sensor type for sensing a given air quality parameter. Each sensor module 140 provides digital measurement data as an output signal. Each sensor module 140 is equipped with a universal connector to be coupled to a matching receptacle 134 formed on the printed circuit board 132. The printed circuit board 132 includes a set of matching receptacles 134 to receive one or more sensor modules 140. In the present embodiment, the universal connector is an USB connector. As thus constructed, base unit 120 can be configured to include sensor modules of the desired sensor types. The configurable base unit 120 can be configured with sensor modules of the same sensor type or sensor modules of different sensor types. Furthermore, sensor modules 140 with universal connectors are removably attached to the base unit so that a base unit can be readily reconfigured by removing and replacing the sensor modules. For example, a sensor module may be replaced with a new sensor module when malfunctioning is detected; or a sensor module of one sensor type may be replaced with a sensor module of a different sensor type to monitor a different air quality parameter of interest.

Each of the matching receptacles 134 is coupled to a data bus formed on the printed circuit board 132 which connects to the controller 180. A sensor module 140 coupled to a matching receptacle communicates with the controller 180 through the data bus. Regardless of the number and types of sensor modules incorporated in a base unit, controller 180 controls and coordinates the transfer of measurement data from each of the sensor module to the data network and onto the central server.

Figure 3:
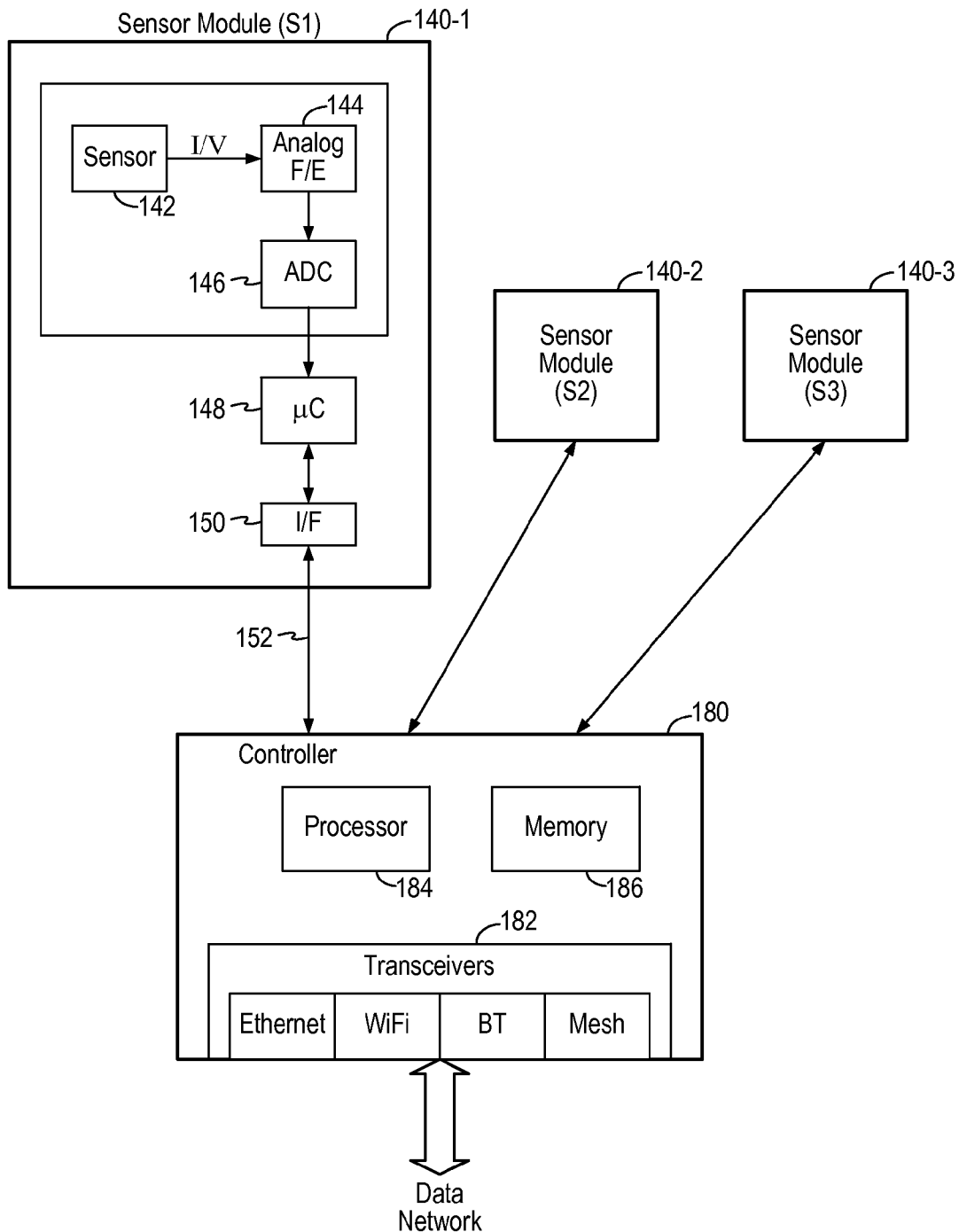
FIG. 3 illustrates a functional block diagram of a base unit in embodiments of the present invention.

FIG. 3 illustrates a functional block diagram of a base unit in embodiments of the present invention. Referring to FIG. 3, a base unit 120 (or "a sensor node") includes a controller 180 in communication with one or more sensor modules 140 and configured to control the operation of the base unit. In the present illustration, the base unit includes three sensor modules 140-1 to 140-3. Each sensor module 140 provides digital measurement data to controller 180 through a data bus 152. In one embodiment, data bus 152 is a serial data bus.

Controller 180 includes a processor 184, a memory 186 and a set of transceivers 182. Controller 180 communicates with each sensor module and coordinates the receipt and transfer of digital measurement data from the sensor modules to the data network. In the present embodiment, controller 180 includes a set of transceivers 182 to provide both wired and wireless communication. In this manner, when base unit 120 is deployed at an installation, the base unit may communicate with a data network using any one of a variety of communication protocols that may be available at that installation. In the present embodiment, controller 180 includes transceivers supporting Ethernet, WiFi, Bluetooth and wireless mesh networking. In other embodiments, controller 180 may support other wired or wireless communication protocols, such as ZigBee or other low power short-range wireless communication protocols.

Sensor module 140 includes a sensor 142 of a specific sensor type for measuring a given air quality parameter. For example, sensor 142 may be a sensor to measure contaminants in the air, such as a carbon monoxide (CO) sensor, an ozone ($O_3$) sensor, a sulphur dioxide ($SO_2$) sensor, or a carbon dioxide ($CO_2$) sensor. Sensor 142 may also be a sensor for measuring particulate matter in the air. Sensor 142 typically provides a current value or a voltage value as an analog output signal. The analog output signal is coupled to an analog front-end circuit 144 which amplifies and conditions the analog output signal. The amplified analog output signal is then provided to an analog-to-digital converter (ADC) 146 to be digitized into a digital sensor output signal. The digital sensor output signal is provided to a microcontroller 148 which communicates with an interface 150 to transmit digital sensor output signal onto the data bus 152. In the present embodiment, microcontroller 148 formats the digital sensor output signal as a serial data stream to be transmitted on the data bus 152. The configuration of sensor module 140 in FIG. 2 is illustrative only and is not intended to be limiting. The exact configuration of sensor module 140 is not critical to the practice of the present invention as long as the sensor module provides digital sensor output signal on a data bus to the controller 180. In other embodiments, the sensor 142 may provide a digital sensor output signal directly. In that case, sensor module 140 does not need to include an analog front-end circuit or an ADC.

As thus configured, each of sensor modules 140-1 to 140-3 measures an air quality parameter specified by the sensor 142. Each sensor module 140-1 to 140-3 provides digital sensor output signal to controller 180. Controller 180 in the base unit 120 receives the digital sensor output signals from the one or more sensor modules 140-1 to 140-3. Controller 180 may store the digital sensor output signals in memory 186 pending transfer to the central server. Controller 180 connects to the data network through the one of communication protocols supported by transceivers 182. Controller 180 operates to transfer the digital sensor output signals as the raw sensor data to the central server for further processing. It is instructive to note that controller 180 does not modify or calibrate the digital sensor output signals and no calibration data associated with the sensors 142 is stored in the base unit.

Referring to FIGS. 1-3, in distributed sensor system 100, a number of sensor nodes 120 may be deployed in an installation. Each of the sensor nodes provides raw sensor data of the measurements it has taken to the central server. Distributed sensor system 100 implements a centralized backend calibration scheme to perform calibration of the raw sensor data at the central server to relieve each sensor node from the burden of storing calibration data and calibrating the measurement data. The centralized backend calibration scheme also has the benefit of enhancing sensor data integrity as the raw sensor data can be calibrated using corrected or updated calibration data in the future.

In embodiments of the present invention, the central server 102 stores calibration data for all of the sensors deployed in the installation in the database 106. The calibration data for the sensors may originate from the manufacturer. A sensor may be provided with a set of calibration data, e.g. gain and offset correction values, during final testing of the sensor at the manufacturing site. A sensor may also be tested before deployment or at deployment to obtain a set of calibration data for that sensor. In embodiments of the present invention, a set of calibration data for a sensor is identified by a sensor identifier (sensor ID) and a board identifier (board ID) so that each set of calibration data is uniquely associated with a specific sensor connected to a specific printed circuit board of a sensor node. Furthermore, the raw sensor data provided by each sensor in a sensor node is similarly identified so that each set of raw sensor data is uniquely associated with a specific sensor on a specific printed circuit board of a sensor node. For instance, the controller 180 appends the board ID and the sensor ID to the digital sensor output signal for each sensor module before the digital sensor output signal is transmitted to the central server. In this manner, when the raw sensor data is transmitted to the central server, the raw sensor data can be readily paired with the associated calibration data through the board identifier and the sensor identifier.

As shown in FIG. 2, a sensor node 120 includes a printed circuit board 132 having a controller 180 formed thereon. The board ID is used to uniquely identify a printed circuit board 132 and the controller 180 formed thereon in a base unit. In other words, the board ID uniquely identifies a base unit or a sensor node. In one embodiment, the board ID is the MAC address assigned to the printed circuit board. The sensor ID uniquely identifies a sensor module 140 or a sensor in the sensor module 140. In one embodiment, the sensor ID is the serial number of the sensor in a sensor module 140. Thus, by using the board ID and the sensor ID, the calibration data and raw sensor data for a sensor incorporated in a sensor node 120 can be uniquely identified. The combination of the board ID and the sensor ID identifies a specific sensor incorporated in a specific sensor node having the specific board ID. More importantly, a sensor module 140 may be removed from one sensor node and incorporated into another sensor node. The raw sensor data for that sensor module will now be associated with a new board ID even though the sensor ID remains the same. By identifying the sensor data (raw sensor data or calibration data) using both the board ID and the sensor ID, traceability of the sensor data for a sensor is maintained regardless of which sensor node the sensor is incorporated in.

FIG. 4 illustrates the organization of a calibration data table in embodiments of the present invention. The calibration data table may be stored in the calibration data base 106 in the central server 102. Referring to FIG. 4, a calibration data table 200 includes multiple entries of calibration data where each entry is identified by a sensor ID and a board ID. For each entry of a given sensor ID and a given board ID, a set of calibration data values for that sensor is stored. In some embodiments, each entry is also associated with a valid date range and a calibration timestamp indicating the day range or the time range when the calibration data is considered valid. For example, the distributed sensor system 100 may perform a calibration of certain sensors once a week. In that case, the calibration data for that sensor will be given a valid date range (start date and end date) and the date the calibration is taken is recorded in the time stamp. If, for some reason, a week is passed and re-calibration was not performed, the central server would know from the valid date range in table 200 that the calibration data for that sensor has expired.

In embodiments of the present invention, the calibration data values for a sensor include one or more calibration terms, including, but not limited to, a gain correction value, an offset correction value, a slope correction value, and a non-linear scaling value. The calibration terms may further include a leakage current correction value, a temperature compensation factor, and ADC settings. In some applications, the calibration data table may be set up to include a given set of calibration terms, such as gain and offset correction and a new calibration term is later found to improve the accuracy of the sensor measurements. For example, a correction term for the ADC gain may be introduced to improve the accuracy of the sensor measurements. In that case, the calibration data table 200 may be updated to include the new calibration term. The central server can regenerate the calibrated sensor data using the raw sensor data stored in the sensor data database 108 and the updated calibration data stored in the calibration data database 106 for each affected sensor. In this manner, the centralized backend calibration scheme enables accurate historic sensor data analysis.

Calibration data table 200 in FIG. 4 is illustrative only. In other embodiments, the calibration data table may store additional data associated with each sensor ID. For example, the calibration data table may include data identifying the sensor type or other reference information. The calibration data table may further include a valid indicator to indicate whether the calibration data for that sensor ID and that board ID should be used for calibrating raw sensor data. An alternate embodiment of a calibration data table is shown in FIG. 8.

Figure 5:
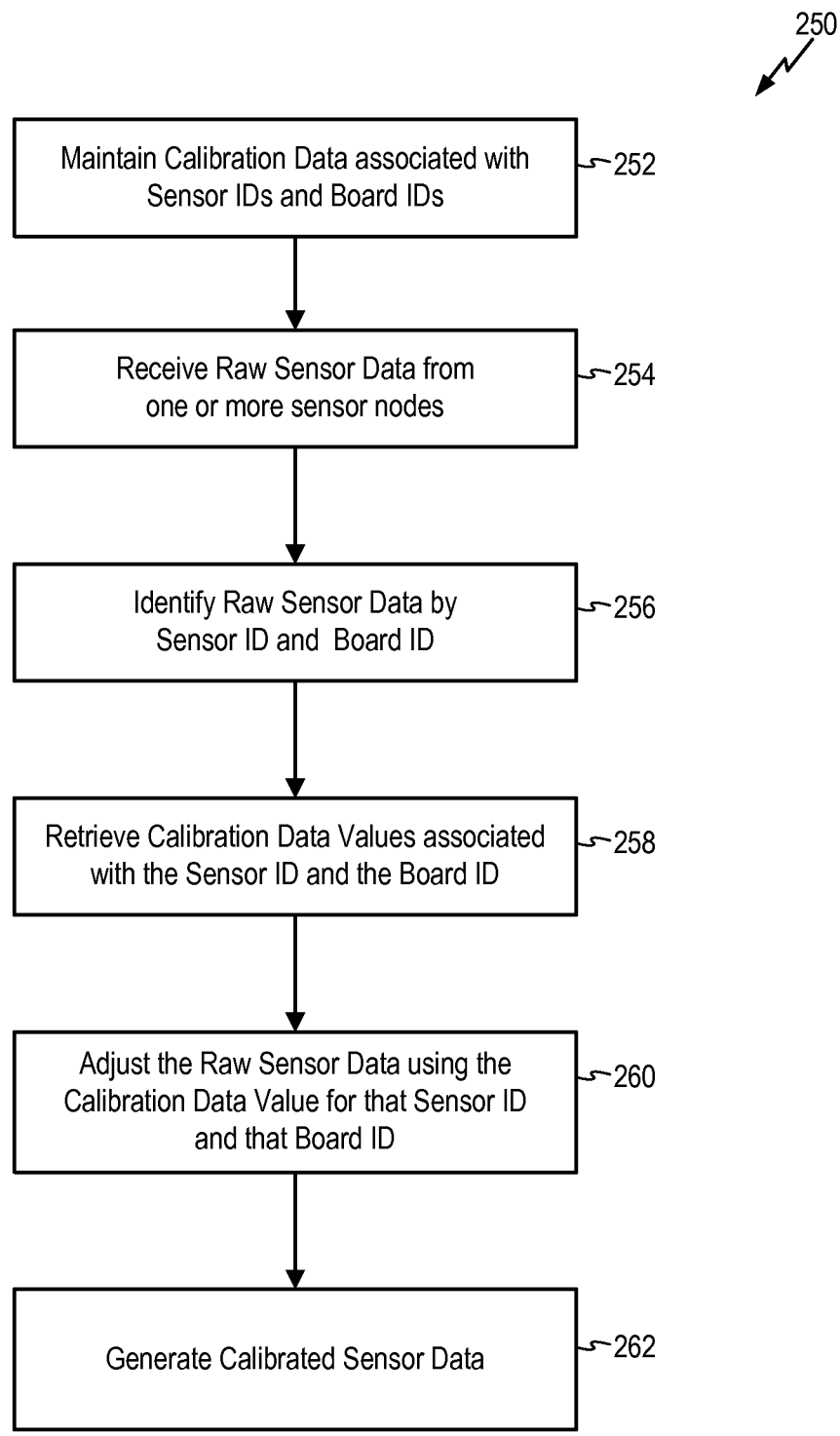
FIG. 5 is a flow chart illustrating a centralized backend calibration method in embodiments of the present invention.

FIG. 5 is a flow chart illustrating a centralized backend calibration method in embodiments of the present invention. Referring to FIG. 5, a centralized backend calibration method 250 may be implemented in the central server 102 in the distributed sensor system 100 for generating calibrated sensor data from raw sensor data received from one or more sensor nodes in the installation. At 252, method 250 maintains calibration data for each sensor in each sensor node in system 100. In one embodiment, the calibration data is stored in the calibration data database 106 and the calibration data is maintained in a calibration data table. Each entry of the calibration data is identified by the sensor ID and the board ID. At 254, central server 102 receives raw sensor data, in the form of digital sensor output signals, from one or more sensor nodes over the data network. At 256, the data processor 104 in the central server 102 identifies the raw sensor data by the sensor ID and the board ID associated with each piece of raw sensor data. Method 250 may store the raw sensor data in the sensor data database 108.

At 258, based on the identified sensor ID and the board ID, the data processor 104 retrieves the calibration data values associated with the sensor ID and the board ID. At 260, the data processor 104 then adjusts or modifies or calibrates the raw sensor data using the calibration data values retrieved for that sensor ID and that board ID. In this manner, method 250 generates calibrated sensor data (262). The calibrated sensor data may be stored in the sensor data database 108.

Method 250 in FIG. 5 describes the backend calibration method for generating calibrated sensor data for raw sensor data received from one or more sensor nodes. Method 250 may also be applied to perform historical sensor data analysis. That is, for raw sensor data that is stored in the sensor data database, method 250 can be applied to recalculate the calibrated sensor data, such as when the calibration data values for one or more sensors have been updated. In that case, instead of receiving the raw sensor data from the sensor nodes, method 250 retrieves the raw sensor data for a sensor ID and a board ID stored in the sensor data database. The retrieved raw sensor data can then be paired with calibration data values stored in the calibration data database through the sensor ID and the board ID. The data processor 104 generates updated calibrated sensor data from the retrieved raw sensor data and updated calibration data values.

In the distributed sensor system of the present invention, the accuracy of the sensor measurements is largely dependent on the accuracy of the calibration data for each sensor. As sensor performance has a tendency to drift over time, calibration data obtained at one point in time may become inaccurate over time and introduces error to the calibrated sensor data. Therefore, it is often necessary to perform recalibration of sensors periodically to update the calibration data values for the sensors. In embodiments of the present invention, the distributed sensor system implements one or more sensor calibration methods to facilitate recalibration of the sensors in the base units in an installation to ensure the accuracy of the calibration data in the central server.

In one embodiment, the distributed sensor system implements an in-situ golden sensor calibration method using a "golden" sensor or a reference sensor. In the present description, a "golden sensor" or a "reference sensor" refers to a sensor with known and verified performance characteristics to which another sensor of the same type can be tested or compared against. Referring again to FIG. 2, a base unit 120 includes a data port 137 which may be used to facilitate the in-situ golden sensor calibration. In embodiments of the present invention, a sensor module containing a golden sensor of the same sensor type as one of the sensor modules in the base unit is connected to the data port 137. In some cases, the golden sensor should be placed near the module under test for some time period to allow the golden sensor to acclimate to the same environmental condition as the module under test.

With a golden sensor thus coupled, the golden sensor takes sensor measurement data which is transmitted to the central server through the operation of controller 180 with the sensor ID of the golden sensor and the board ID of the base unit 120. The central server identifies the raw sensor data received as the golden or reference sensor measurement originated from a golden sensor by the sensor ID and also identifies the base unit to which the golden sensor is attached by the board ID. Meanwhile, the central server also receives raw sensor data as test sensor measurement from the sensor under test in the base unit identified by the sensor ID of the sensor under test and the board ID. Because the golden sensor is placed in the vicinity of the sensor under test, the sensor measurements generated by the golden sensor and the sensor under test should be about the same. The central server, receiving the golden sensor measurement and the test sensor measurement can thus derive the correction factors to be applied to the sensor under test to improve the accuracy of the sensor measurements. The updated calibration data values are stored in the calibration data table for the sensor under test, as identified by the sensor ID and the board ID.

When the in-situ golden sensor calibration method is used, each sensor module in a base unit is calibrated in turn by supplying a golden sensor module and coupling the golden sensor module to the data port 137. When the base unit includes multiple sensor modules, the one-by-one calibration method may become impractical. In another embodiment of the present invention, the distributed sensor system implements an in-situ golden base unit calibration method using a "golden" base unit or a reference base unit. In the present description, a "golden base unit" or a "reference base unit" refers to a base unit including a given set of sensor modules with known and verified performance characteristics to which another base unit with the same sensor modules or a subset of the sensor modules can be tested or compared against. When a golden base unit is used, the golden base unit is placed in the vicinity of a base unit under test. In some cases, the golden base unit should be placed near the base unit under test for some time period to allow the golden base unit to acclimate to the same environmental condition as the base unit under test.

With the golden base unit thus situated, the golden base unit takes sensor measurement data which is transmitted to the central server through the operation of controller 180 with the sensor ID of each of the sensor modules thereon and the board ID of the golden base unit. The central server identifies the raw sensor data received as golden or reference sensor measurements originated from a golden base unit by the sensor ID of the sensor modules and the board ID of the golden base unit. Meanwhile, the central server also receives raw sensor data as test sensor measurements from the sensor modules of the base unit under test identified by the sensor ID and the board ID of the base unit under test. Because the golden base unit is placed in the vicinity of the base unit under test, the sensor measurements generated by the golden base unit and the base unit under test should be about the same. The central server, receiving the golden sensor measurements of the golden base unit and the test sensor measurements of the base unit under test can thus derive the correction factors to be applied to the sensors in the base unit under test to improve the accuracy of the sensor measurements. The updated calibration data values are stored in the calibration data table for the sensor modules in the base unit under test, as identified by the sensor ID and the board ID.

The in-situ golden base unit calibration method is applied to calibrate all of the sensor modules in a base unit collectively. In some embodiments, when multiple base units are deployed in close vicinity to each other, the same golden base unit can be used to calibrate a group of the base units that are installed within a given distance from the golden base unit. In some embodiments, each base unit is equipped with a GPS positioning device and the central server uses the GPS positioning data of each base unit to determine the group of base units that is in close proximity to the golden base unit.

Figure 6:
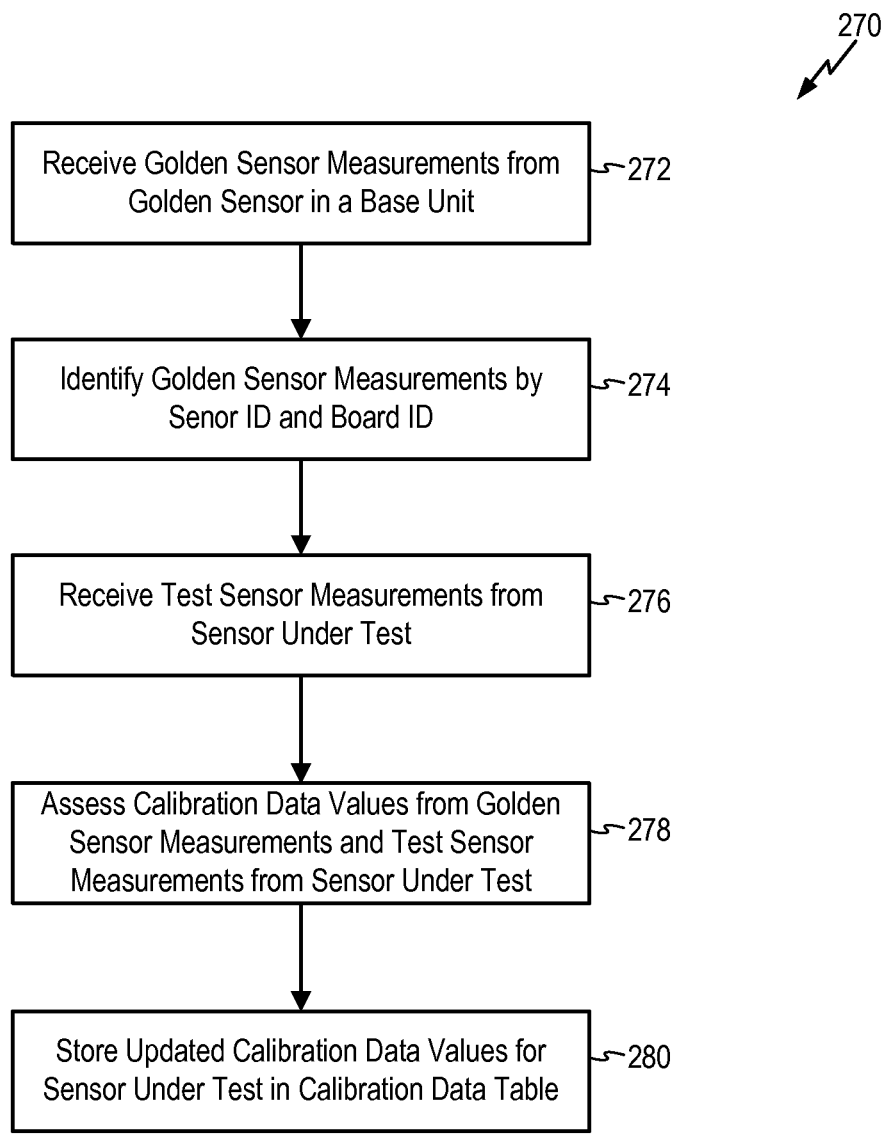
FIG. 6 is a flow chart illustrating an in-situ calibration method in embodiments of the present invention.

FIG. 6 is a flow chart illustrating an in-situ calibration method in embodiments of the present invention. The in-situ calibration method can be implemented using a golden sensor or a golden base unit as described above. Referring to FIG. 6, an in-situ calibration method 270 starts at 272 when the central server receives sensor measurements that are identified as being from a golden sensor, which can be a golden sensor module connected to a base unit under test or a golden sensor in a golden base unit. At 274, the central server identifies the sensor measurements as golden sensor measurements by the sensor ID and the board ID. In the case of a golden sensor calibration, the sensor ID identifies the golden sensor while the board ID identifies the base unit to which the golden sensor is attached. In the case of a golden base unit calibration, the sensor ID and the board ID identifies the golden base unit.

At 276, the central server receives test sensor measurements from the sensor under test. In the case of a golden sensor calibration, the sensor ID identifies the sensor under test while the board ID identifies the base unit to which the golden sensor is attached. In the case of a golden base unit calibration, the sensor ID and the board ID identifies a sensor module in the base unit under test. The base unit under test can be one or more base units that are located in close physical proximity to the golden base unit. At 278, method 270 assesses the calibration data values from the golden sensor measurements and the test sensor measurement from the sensor under test. At 280, method 270 stores the updated calibration data values for the sensor under test in the calibration data table.

In one embodiment, a multi-point calibration is performed. That is, multiple golden sensor measurements and multiple test sensor measurements for the sensor under test are taken under different environmental conditions, for example, during the day and during the night, during work hours or during off-work hours. Calibration data values obtained from multiple sensor measurements usually give better results.

In another embodiment, a single-point calibration is performed at high frequency. That is, the calibration data are computed from golden sensor measurement taken under one environmental condition but the method 270 is repeated periodically and at high frequency. By updating the calibration data frequently, the accuracy of the calibration data is also improved.

In embodiments of the present invention, a golden base unit and a base unit under test are connected in a daisy chain or a master-slave configuration. In this manner, the sensor data from the base unit under test is automatically associated with the golden sensor data so that the central server can readily identify the sensor being calibrated and the golden sensor data to use for the calibration. When a golden base unit is connected in a master-slave configuration with a base unit under test, golden sensor measurements are transmitted through the base unit under test to the central server. The controller in the base unit under test appends its board ID ("test board ID") to sensor ID/boardID of the golden base unit so that the central server can identify the golden sensor measurements as being provided through the base unit under test. In this manner, any subsequent sensor measurement received with the same test board ID identifies those sensor measurements as being from the base unit under test.

Figure 7:
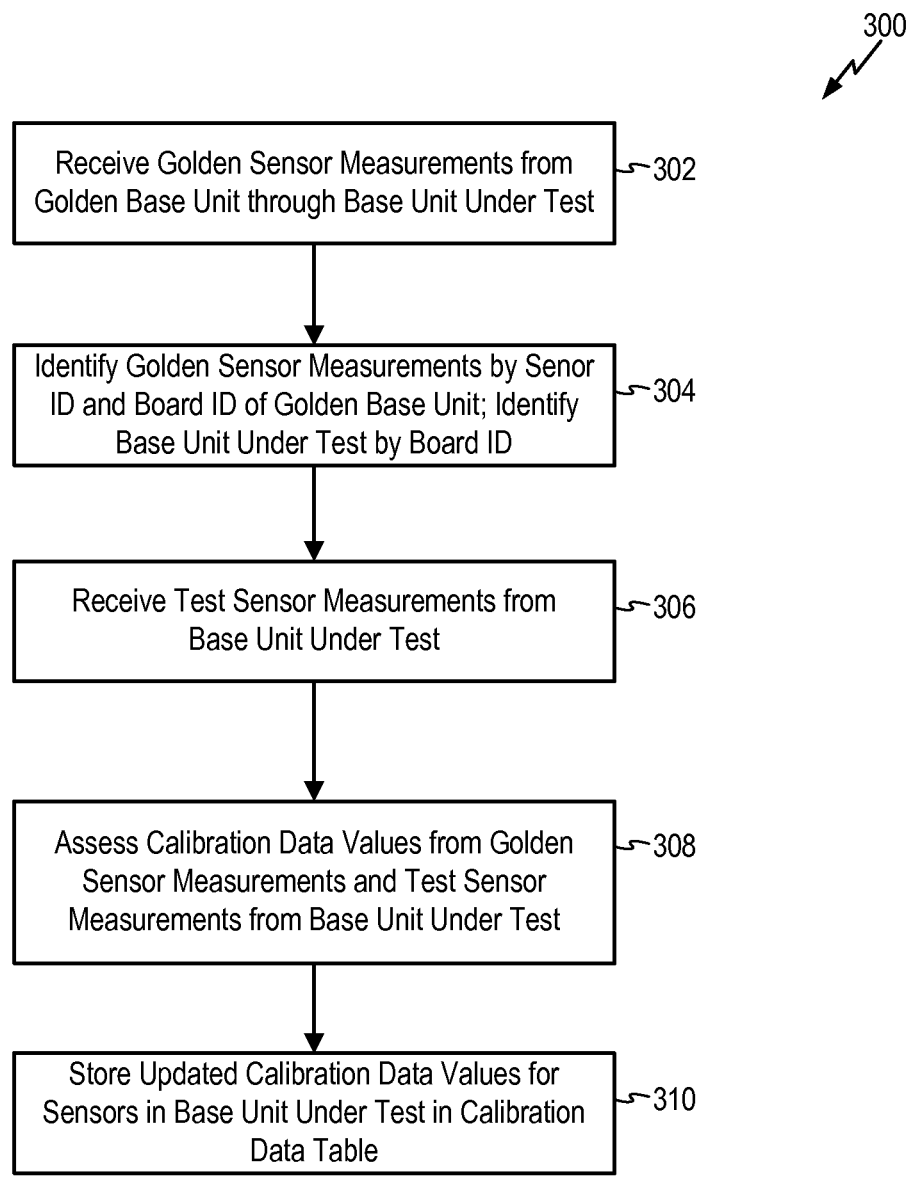
FIG. 7 is a flow chart illustrating a daisy-chained in-situ calibration method in embodiments of the present invention.

FIG. 7 is a flow chart illustrating a daisy-chained in-situ calibration method in embodiments of the present invention. Referring to FIG. 7, a daisy-chained in-situ calibration method 300 starts at 302 when the central server receives sensor measurements that are identified as being from a golden base unit transmitted through the base unit under test. At 304, the central server identifies the sensor measurements as golden sensor measurements by the sensor ID and the board ID of the golden base unit. The central server further identifies the base unit under test by the board ID appended to the golden sensor measurements. The board ID of the base unit under test will be referred to as the "test board ID."

At 306, the central server receives sensor measurements from the base unit under test as the test sensor measurements. At 308, method 300 assesses the calibration data values from the golden sensor measurements and the test sensor measurement from the base unit under test. At 310, method 300 stores the updated calibration data values for the sensor modules in the base unit under test in the calibration data table. When the golden sensor measurements are funneled through the base unit under test to be transmitted to the central server, the golden sensor measurements and the sensor measurements for the base unit under test are automatically associated with each other so that calibration data for the base unit under test can be readily updated.

According to other aspects of the present invention, the distributed sensor system may perform calibration of the sensors in the base units without the use of any reference sensor or reference base unit. In one embodiment, the distributed sensor system performs crowd-sourced calibration based on the network effect of a group of neighboring sensors of the same sensor type. In the distributed sensor system, there is usually an array of base units deployed in an installation when a group of the base units are in close enough vicinity of each other to measure similar environmental conditions. The performance of a group of neighboring base units with expected similar sensor measurements can be used to calibrate the sensors in that group of base units. In one embodiment, neighboring base units with expected similar sensor measurements are designated as belonging to a calibration group. The central server compares the sensor measurements of a given sensor in the base units of the calibration group. Based on the analysis of the sensor measurements from the calibration group, the central server may determine that the calibration data values for sensors in some of the base units may need to be compensated. The central server may then update the calibration data values for the sensors in the base units and store the updated calibration data in the calibration data database.

According to another aspect of the present invention, the distributed sensor system performs calibration of the sensors in a base unit using sensor data associated with ambient conditions collected in the same base unit. In one embodiment, a base unit includes a temperature sensor and/or a humidity sensor. Most sensors for measuring air quality parameters have a temperature dependency and/or humidity dependency. In embodiments of the present invention, the central server collects temperature and/or humidity data recorded by a base unit and use the temperature and/or humidity data to calibrate the sensor measurements generated by the air quality sensors in the same base unit. In this manner, the temperature and/or humidity dependency can be removed from the sensor measurements of the base unit and the sensor measurements can be made more accurate.

In yet another aspect of the present invention, the distributed sensor system performs calibration of the sensors in a base unit based on sensor cross-sensitivity. Some air quality sensors have cross-sensitivity with the potential to respond to contaminants other than the target contaminant. Thus, two sensor types designed for two different target contaminants may respond to some degree to the same contaminant in the air. For example, ozone sensor and nitric oxide sensor have a given degree of sensor cross-sensitivity. In that case, in a base unit equipped with an ozone sensor and a nitric oxide sensor, the sensor measurements from both sensors should correlate with each other to some degree as a result of the cross-sensitivity. That is, if the sensor measurement from the ozone sensor indicated increased detected level, the nitric oxide sensor should also indicate a similar increase in detected level. In embodiments of the present invention, the central server monitors and calibrates sensor performances by analyzing sensor measurements from sensors with known cross-sensitivity. In one embodiment, the central server receives sensor measurements from a first group of sensors of a first sensor type and sensor measurements from a second group of sensors of a second sensor type having a sensor cross-sensitivity with the first sensor type. The central server generates compensation to the calibration data based on the sensor measurements of the first and second group of sensors.

Furthermore, in embodiments of the present invention, the central server receives sensor measurements from a first group of sensors of a first sensor type and sensor measurements from a second group of sensors of a second sensor type having a sensor cross-sensitivity with the first sensor type. The central server determines specification of the different gases, that is, the concentration of individual gases, based on the sensor measurements and the sensors cross-sensitivity characteristics. In one embodiment, by analyzing the sensor measurements based on the known cross-sensitivity, the concentration of a given gas can be determined.

In yet another aspect of the present invention, the distributed sensor system performs calibration of the sensors based on known environmental conditions. In particular, the central server performs calibration of a sensor by analyzing sensor measurements from the sensor that were taken under the same environment conditions over a period of time. For example, a base unit is installed in an office and the office is unoccupied between the hours of midnight and dawn. The central server may collect sensor measurements from the sensor at the same time (e.g. 2 am) over a period of time (e.g. 6 months). The central server analyzes sensor measurements taken from the sensor under the same environmental condition over a period of time to determine a trend. The central server determines compensation to the calibration data of the sensor based on the trend analysis.

In some embodiments, a base unit stores sensor calibration data for the sensor modules incorporated therein in the base unit's local memory. Referring to FIG. 3, the base unit 120 may store calibration data for the sensor modules 140-1 to 140-3 in the memory 186 on controller 180. The controller still operates to transmit raw sensor data to the central server. However, in embodiments of the present invention, the controller 180 performs local calibration of the raw sensor data and generates locally calibrated sensor data. The locally calibrated sensor data may be stored in memory 186.

Although the foregoing embodiments have been described in some detail for purposes of clarity of understanding, the invention is not limited to the details provided. There are many alternative ways of implementing the invention. The disclosed embodiments are illustrative and not restrictive.

The invention claimed is:

1. A method of calibrating sensors in a distributed sensor system comprising a plurality of spatially distributed base units in communication with a central server over a data network, each base unit comprising one or more sensors configured to measure an air quality parameter, the method comprising:

maintaining on the central server calibration data for sensors in the distributed sensor system in a calibration data database, the calibration data for a sensor being associated with a sensor identifier uniquely identifying the sensor in a base unit and a board identifier uniquely identifying the base unit in the system;

receiving at the central server a reference sensor measurement from a reference sensor associated with a first base unit;

identifying at the central server the reference sensor measurement by a sensor identifier uniquely identifying the reference sensor associated with the first base unit and a board identifier uniquely identifying the first base unit;

receiving at the central server a test sensor measurement from a first sensor under test;

identifying at the central server the test sensor measurement by a sensor identifier uniquely identifying the first sensor and a board identifier uniquely identifying a base unit in which the first sensor is installed;

determining at the central server calibration data values for the first sensor under test using the reference sensor measurement and the test sensor measurement; and storing in the calibration data database on the central server updated calibration data values for the first sensor under test.

2. The method of claim 1, wherein the first sensor under test is provided in the first base unit and the reference sensor is coupled to a data port of the first base unit, and the method further comprises:

identifying at the central server the test sensor measurement by a sensor identifier uniquely identifying the first sensor under test and a board identifier uniquely identifying the first base unit.

3. The method of claim 1, wherein the first base unit comprises a reference base unit and the first sensor under test is formed in a second base unit, the reference base unit being placed in the vicinity of the second base unit, and the method further comprises:
  identifying at the central server the test sensor measurement by a sensor identifier uniquely identifying the first sensor under test and a board identifier uniquely identifying the second base unit.

4. The method of claim 3, further comprising:
  receiving at the central server test sensor measurements from a plurality of sensors under test in a plurality of base units, the plurality of base units being positioned within a given distance from the reference base unit;
  determining at the central server calibration data values for the plurality of sensors under test using the reference sensor measurement and the test sensor measurements for each of the sensors under test; and
  storing at the central server updated calibration data values for the plurality of sensors under test.

5. The method of claim 4, further comprising:
  determining at the central server a base unit with a sensor under test to be within a given distance from the reference base unit using positioning data from the base unit and the reference base unit.

6. The method of claim 1, wherein the first base unit comprises a reference base unit and the first sensor under test is formed in a second base unit, and the method further comprises:
  connecting the reference base unit in a master-slave configuration with the second base unit; and
  transmitting to the central server the reference sensor measurement through the second base unit.

7. The method of claim 6, further comprising:
  identifying at the central server the reference sensor measurement by a sensor identifier uniquely identifying the reference sensor in the first base unit, a board identifier uniquely identifying the reference base unit, and a test board identifier uniquely identifying the second base unit;
  identifying at the central server the test sensor measurement by a sensor identifier uniquely identifying the first sensor under test and a board identifier uniquely identifying the second base unit; and
  associating at the central server the reference sensor measurement and the test sensor measurement from the first sensor under test using the board identifier of the second base unit.

8. The method of claim 1, further comprising:
  receiving at the central server reference sensor measurements from the reference sensor taken at a plurality of environmental conditions;
  receiving at the central server test sensor measurements from the first sensor under test taken at the plurality of environmental conditions; and
  determining at the central server calibration data values for the first sensor under test using the reference sensor measurements and the test sensor measurements taken at the plurality of environmental conditions.

9. A method of calibrating sensors in a distributed sensor system comprising a plurality of spatially distributed base units in communication with a central server over a data network, each base unit comprising one or more sensors configured to measure an air quality parameter, the method comprising:
  maintaining on the central server calibration data for sensors in the distributed sensor system in a calibration data database, the calibration data for a sensor being associated with a sensor identifier uniquely identifying the sensor in a base unit and a board identifier uniquely identifying the base unit in the system;
  receiving at the central server sensor measurements from sensors of the same sensor type in neighboring base units belonging to a calibration group, the sensors in the calibration group being subjected to similar environmental conditions and having expected similar sensor measurements;
  analyzing at the central server sensor measurements for the sensors in the calibration group;
  determining at the central server calibration data values for one or more sensors in the calibration group using the sensor measurements received from the calibration group; and
  storing in the calibration data database on the central server updated calibration data values for the one or more sensors.

10. The method of claim 9, further comprising:
  associating at the central server neighborhood base units in the calibration group when sensors of the same sensor type in the base units are expected to generate similar sensor measurements.

11. A method of calibrating sensors in a distributed sensor system comprising a plurality of spatially distributed base units in communication with a central server over a data network, each base unit comprising one or more sensors configured to measure an air quality parameter, the method comprising:
  maintaining on the central server calibration data for sensors in the distributed sensor system in a calibration data database, the calibration data for a sensor being associated with a sensor identifier uniquely identifying the sensor in a base unit and a board identifier uniquely identifying the base unit in the system;
  receiving at the central server a sensor measurement associated with air quality from a first sensor in a first base unit;
  receiving at the central server a sensor measurement associated with an ambient condition from the first base unit;
  determining at the central server calibration data values for the first sensor using the sensor measurement associated with the ambient condition; and
  storing in the calibration data database on the central server updated calibration data values for the first sensor.

12. The method of claim 11, wherein receiving at the central server a sensor measurement associated with an ambient condition from the first base unit comprises:
  receiving at the central server a sensor measurement associated with temperature from the first base unit.

13. The method of claim 11, wherein receiving at the central server a sensor measurement associated with an ambient condition from the first base unit comprises:
  receiving at the central server a sensor measurement associated with humidity from the first base unit.

14. A method of calibrating sensors in a distributed sensor system comprising a plurality of spatially distributed base units in communication with a central server over a data network, each base unit comprising one or more sensors configured to measure an air quality parameter, the method comprising:
  maintaining on the central server calibration data for sensors in the distributed sensor system in a calibration data database, the calibration data for a sensor being associated with a sensor identifier uniquely identifying the sensor in a base unit and a board identifier uniquely identifying the base unit in the system;

associating at the central server a first sensor in a base unit with a second sensor in the base unit having sensor cross-sensitivity;

receiving at the central server sensor measurements from the first sensor and the second sensor;

analyzing at the central server sensor measurements from the first sensor and the second sensor;

determining at the central server calibration data values for the first and second sensors based on the sensor measurements from the first and second sensors with known sensor cross-sensitivity; and storing in the calibration data database on the central server updated calibration data values for the first and second sensors.

15. The method of claim 14, further comprising:

determining at the central server a concentration of a gas measured by the first sensor based on the sensor measurements from the first and second sensors and the sensor cross-sensitivity characteristics.

16. A method of calibrating sensors in a distributed sensor system comprising a plurality of spatially distributed base units in communication with a central server over a data network, each base unit comprising one or more sensors configured to measure an air quality parameter, the method comprising:

maintaining on the central server calibration data for sensors in the distributed sensor system in a calibration data database, the calibration data for a sensor being associated with a sensor identifier uniquely identifying the sensor in a base unit and a board identifier uniquely identifying the base unit in the system;

receiving at the central server a plurality of sensor measurements from a first sensor in a first base unit under a known environment condition over a period of time;

analyzing at the central server the plurality of sensor measurements to determine a trend;

determining at the central server calibration data values for the first sensor based on the trend analysis of the plurality of sensor measurements received over the period of time; and storing in the calibration data database on the central server updated calibration data values for the first sensor.

* * * * *

UNITED STATES PATENT AND TRADEMARK OFFICE
CERTIFICATE OF CORRECTION

| | |
|---|---|
| PATENT NO. | : 9,291,608 B2 |
| APPLICATION NO. | : 13/800199 |
| DATED | : March 22, 2016 |
| INVENTOR(S) | : Herzl et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Fifth Day of July, 2016

Michelle K. Lee
*Director of the United States Patent and Trademark Office*